(12) United States Patent
Kehrer et al.

(10) Patent No.: US 8,647,594 B2
(45) Date of Patent: Feb. 11, 2014

(54) WELLPLATE HANDLER SYSTEM FOR A FLOW CYTOMETER

(75) Inventors: Aaron Kehrer, Ypsilanti, MI (US); Nathaniel C. Bair, Ann Arbor, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 1016 days.

(21) Appl. No.: 12/504,571

(22) Filed: Jul. 16, 2009

(65) Prior Publication Data

US 2010/0014947 A1 Jan. 21, 2010

Related U.S. Application Data

(60) Provisional application No. 61/082,045, filed on Jul. 18, 2008.

(51) Int. Cl.
*G01N 35/04* (2006.01)
*G01N 35/08* (2006.01)
*G01N 35/10* (2006.01)

(52) U.S. Cl.
USPC ............. 422/561; 422/65; 422/501; 422/552; 422/553; 73/864.23; 73/864.24

(58) Field of Classification Search
None
See application file for complete search history.

(56) References Cited

U.S. PATENT DOCUMENTS

| | | | |
|---|---|---|---|
| 4,824,641 | A | 4/1989 | Williams |
| 5,138,868 | A | 8/1992 | Long |
| 5,374,395 | A | 12/1994 | Robinson et al. |
| 5,517,867 | A * | 5/1996 | Ely et al. .................... 73/863.85 |
| 5,804,507 | A | 9/1998 | Perlov et al. |
| 6,416,719 | B1 * | 7/2002 | Fawcett et al. ................ 422/561 |
| 2004/0048362 | A1 | 3/2004 | Trulson et al. |
| 2005/0047292 | A1 | 3/2005 | Park et al. |
| 2005/0078299 | A1 | 4/2005 | Fritz et al. |
| 2005/0105091 | A1 | 5/2005 | Lieberman et al. |
| 2006/0216207 | A1 * | 9/2006 | Lehto ............................ 422/100 |
| 2006/0281143 | A1 | 12/2006 | Liu et al. |
| 2007/0059205 | A1 * | 3/2007 | Ganz et al. ...................... 422/63 |
| 2007/0096039 | A1 | 5/2007 | Kapoor et al. |
| 2008/0152542 | A1 | 6/2008 | Ball et al. |
| 2008/0254545 | A1 * | 10/2008 | Kitaoka ......................... 436/47 |
| 2009/0293910 | A1 | 12/2009 | Ball et al. |

FOREIGN PATENT DOCUMENTS

WO 2007/136749 5/2007

* cited by examiner

*Primary Examiner* — P. Kathryn Wright
(74) *Attorney, Agent, or Firm* — Jeffrey Schox

(57) ABSTRACT

A plate handling system for a sampling device with a drawtube that includes a vertical actuation system that adjusts the vertical distance between the drawtube and a sample tray, a horizontal linkage system that positions a sample tray in a horizontal plane, and a drive system that drives the rotational motion of the horizontal linkage system. The horizontal linkage system includes a base arm that rotates about a base joint, and a sample arm that rotates about a sample arm joint on the base arm.

13 Claims, 3 Drawing Sheets

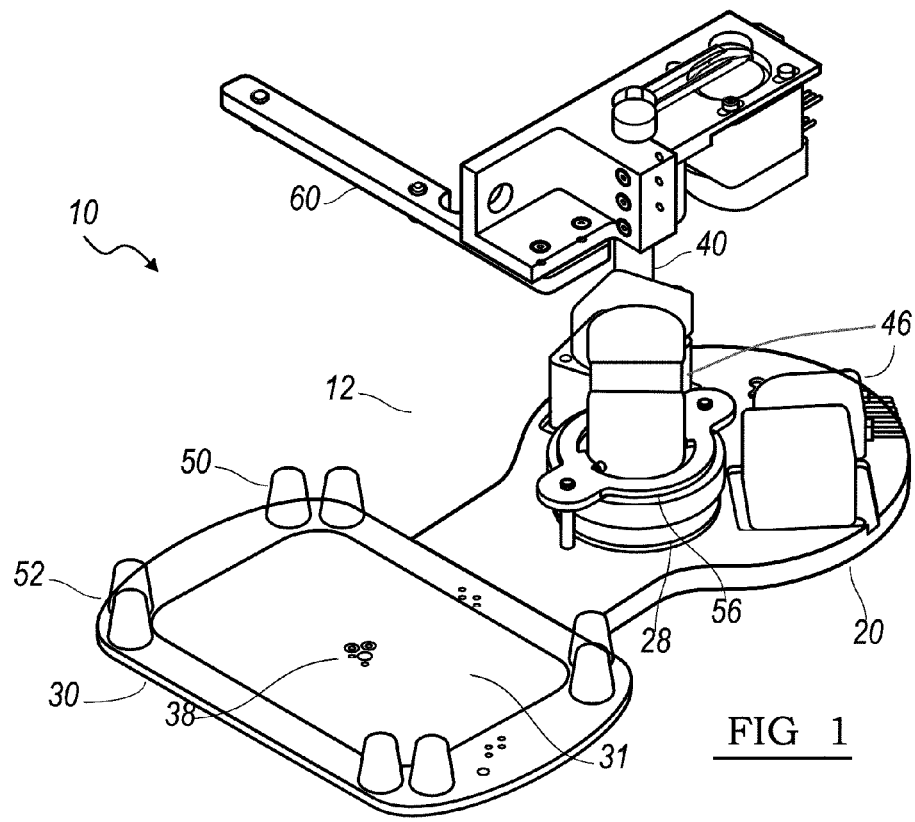
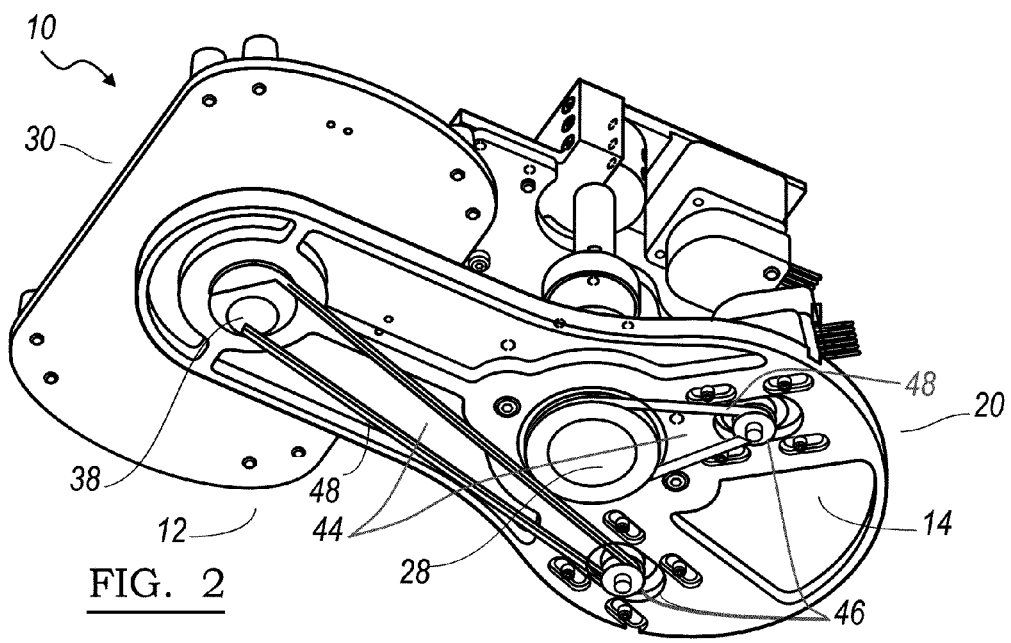

WELLPLATE HANDLER SYSTEM FOR A FLOW CYTOMETER

CROSS-REFERENCE TO RELATED APPLICATIONS

This application claims the benefit of U.S. Provisional Ser. No. 61/082,045 filed on 18 Jul. 2008, which is incorporated in its entirety by this reference.

BACKGROUND

Wellplate handlers are often used to position a wellplate for automated sampling of numerous wells of a wellplate. Wellplate handlers for devices such as flow cytometers typically use lead screws, ball screws, or rack and pinions systems to provide the 2D manipulation of a device. These systems typically maneuver a wellplate linearly along an X axis and an Y axis. While competent in some ways, these systems are slow and require a large dedicated surface area to maneuver over a given area. These systems are also unable to easily sense and adjust to a bent probe, which—if the bent probe reaches an unattended well—can be disastrous to the data of the sampling. Thus there is a need in the automated wellplate handler field to create an improved and useful wellplate handler. This invention provides such a new and useful system and methods.

BRIEF DESCRIPTION OF THE FIGURES

FIG. 1 is perspective view of a preferred embodiment of the invention.

FIG. 2 is a perspective view of the underside of the preferred embodiment of the invention.

DESCRIPTION OF THE PREFERRED EMBODIMENTS

Figure 3:
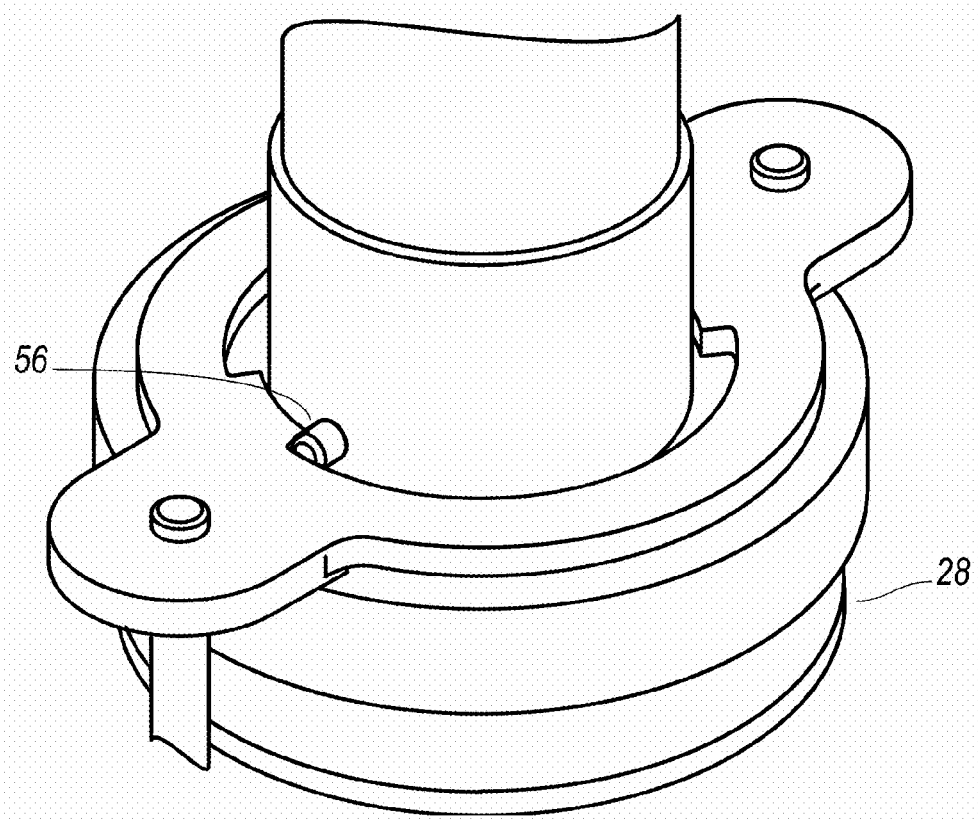
FIG. 3 is a detailed view of an arm positioning peg.

The following description of the preferred embodiments of the invention is not intended to limit the invention to these preferred embodiments, but rather to enable any person skilled in the art to make and use this invention.

1. Plate Handler System

As shown in FIG. 1, the plate handler system 10 of the preferred embodiment functions to move a sample tray to various positions in relationship to a drawtube of a sampling device, in particular a flow cytometer. The plate handler system 10 preferably includes a vertical actuation system 40, a horizontal linkage system 12, and a drive system 14. The vertical actuation system 40 functions to move the contents of a sample tray and a drawtube into and out of contact along a vertical axis. The horizontal linkage system 12 functions to hold a sample tray (e.g., a wellplate) and provide the mechanical structure to translate the sample tray to various positions on a 2D horizontal plane. The drive system 14 functions to drive the rotational movement of the horizontal linkage system 12. The plate handler system lo preferably also includes bumpers 50 and/or a positioning bumper 52. The bumpers 50 function to receive a wellplate and locate the wellplate to a known position on the horizontal linkage system 12. The positioning bumper 52 may additionally function to find the relative position of the drawtube and the sample tray. Although designed for a flow cytometer system such as the flow cytometer system that is disclosed in US Publication No. 2007/0224684 filed on 22 Mar. 2006 and entitled "Transportable Flow Cytometer" (which is incorporated in its entirety by this reference), the plate handler system lo may be used in any suitable environment or for any suitable sampling device.

The vertical actuation system 40 of the preferred embodiment functions to move the contents of the sample tray and a drawtube into and out of contact along a vertical axis. The contents of the sample tray and the drawtube are moved out of contact to allow the horizontal linkage system 12 to move the sample tray along the horizontal plane without interference by the drawtube. The contents of the sample tray and the drawtube are moved vertically into contact when needed, for example when the drawtube draws in a sample fluid from a well of a well plate. The vertical actuation system 40 preferably adjusts the vertical displacement between the horizontal linkage system and the drawtube. The vertical actuation system 40 is preferably capable of adjusting the vertical distance for a continuous displacement range (or a nearly continuous range of positions) to accommodate for a variety of sample trays such as a rack of test tubes or deep-well well plates. For example, a rack of different tubes (such as 12×75 mm, 1.5 mL, 0.5 mL etc.) or even sampling off of a flat surface (no reservoir) may be individually accommodated for by the vertical actuation system 40. The displacement range is preferably a six inch range, but any suitable vertical displacement range may alternatively be used. The vertical actuation system may alternatively have a limited number of discrete displacement heights, such as a sample tray-change height, a clearance height, and a sampling height. The sample tray-change height is preferably where the sample tray and the draw tube are at a maximum vertical displacement, and the height preferably used when changing a sample tray. The clearance height is preferably high enough to move the horizontal linkage system between different samples, but closer to the sample tray for faster sampling operation. The sampling height is preferably where the drawtube and the contents of the sample tray are in contact or alternatively when the drawtube is in contact with the sample fluid. The vertical actuation system 40 may additionally have a sufficiently high resolution of actuation (e.g., <0.5 mm). In one application, a sufficiently high resolution vertical actuation system 50 may be used to sample specific stratified layers in a tube, such as after centrifugation. These different displacement heights or any suitable number of heights may additionally be implemented for operation with the discrete or continuous range. In a preferred embodiment, the vertical actuation system 40 moves the horizontal linkage system 12 vertically upwards towards the drawtube to bring the contents of the sample tray and the drawtube into contact. The vertical actuation system may alternatively be mounted on the horizontal linkage system 12 and move a sample tray upwards. In an alternative embodiment, the vertical actuation system 40 moves the drawtube vertically downward towards to the horizontal linkage system 12 to bring the wellplate and the drawtube into contact. The vertical actuation system 40 of this alternative embodiment additionally may include a flexible tube running from the drawtube to the flow cytometer. The flexible tube functions to maintain the connection of the drawtube 18 connection to the flow cytometer, while providing flexibility so the drawtube can move vertically away from and towards the flow cytometer chassis. The vertical actuation system 40 preferably includes a motor and a lead screw mechanism (or ball screw mechanism) to actuate the horizontal linkage system 12 along a vertical axis. The vertical actuation system 40 alternatively may use solenoids, cams, pistons, belts and pulleys, or any suitable mechanisms to achieve the vertical actuation.

The horizontal linkage system 12 of the preferred embodiment functions as the platform that positions a sample tray along a 2D horizontal plane. The horizontal linkage system 12 is preferably able to position any given well on the sample tray under a drawtube of the sampling device. The horizontal linkage system 12 preferably includes a base arm 20 and a sample arm 30. The horizontal linkage system 12 preferably has at least two rotational degrees of freedom and preferably no linear degrees of freedom. The horizontal linkage system 12 preferably positions the sample tray through rotational motion of the base arm 20 and the sample arm 30. The base arm 20 and sample arm 3o preferably cooperate to form a three bar linkage system with only two rotational degrees of freedom. The three bar linkage is preferably open. As used herein, the term "open" is understood to mean the links of the linkage preferably do not form a closed linkage system where every link is connected to at least two other links. The flow cytometer preferably functions as one link of the three bar linkage, or alternatively the ground or any suitable object may function as a frame or fixed reference link. A second link is preferably the base arm 20 that preferably has two rotational joints and preferably links the sample arm 30 and the flow cytometer (or the frame). The third link is preferably the sample arm 30 rotating about one of the rotational joints of the base arm 20. Additional links may alternatively be included in the horizontal linkage system 12 and the horizontal linkage system 12 may alternatively be open or closed. The base arm 20 and sample arm 30 also cooperate to enable any given sample in a sample tray (e.g., well of a wellplate) to be positioned under the drawtube 18. The base arm 20 and the sample arm 30 preferably rotate independently, with the base arm 20 rotating about one a stationary base arm joint 28 and the sample arm 30 rotating about a sample arm joint 38 on the base arm 20.

The base arm 20 of the horizontal linkage system 12 functions to provide a degree of freedom to the horizontal linkage system 12 in the form of rotation about a fixed point. The base arm 20 further functions to provide the base for the sample arm 30. The base arm 20 is preferably a flat length of rigid material. Preferably, the base arm 20 is made of aluminum. Alternatively, steel, plastic, carbon fiber, or any suitably rigid material may be used for the base arm 20. The base arm 20 includes a base arm joint 28 about which the base arm 20 can rotate. The location of the base arm joint 28 is preferably fixed relative to the flow cytometer. The base arm joint 28 is preferably mounted to the flow cytometer by the fixture 60. The base arm 20 also includes a sample arm joint 38 to function as the point about which the sample arm 30 rotates. The sample arm joint 38 and base arm joint 28 are suitably spaced to allow a sample tray to be maneuvered over the desired area. This spacing between the sample arm joint 38 and the base arm joint 28 is preferably greater than half the length of a sample tray. The length of the base arm 20 is preferably on the order of magnitude of the length of a 96-well well plate to provide sufficient maneuverability of the well plate. The length may alternatively be sized to allow a sample tray to fully rotate about the sample arm joint 38 or any suitable length may be used.

The sample arm 30 of the horizontal linkage system 12 functions to provide a second degree of freedom to the horizontal linkage system 12 in the form of rotation about a fixed point on the base arm 20. The sample arm 30 further functions to hold a received sample tray. The sample arm 30 is preferably a flat length or plate of rigid material. Preferably, the sample arm 30 is made of aluminum. Alternatively, steel, plastic, carbon fiber, or any suitably rigid material may be used for the sample arm 30. The area of the flat portion of the well plate arm 20 is preferably sized to fit a 96-well wellplate, but may alternatively be sized to hold any suitable sample tray. The sample arm 30 also includes the sample arm joint 38 that connects to the base arm 20, as described above. The sample arm joint 38 functions to provide a point about which the sample arm 30 can rotate. The sample arm joint 38 is preferably centrally located on the sample arm 30 such that the sample arm 30 symmetrically rotates about the sample arm joint 38. The preferred embodiment of the sample arm 30 preferably includes a sample tray fixture 31. The sample tray fixture 31 functions to receive a sample tray and position the sample tray to a known position on the sample arm 30. The sample tray fixture 31 is preferably a structure that is apart of or attached to the sample arm 30. The sample tray fixture 31 may alternatively be slot, a hole, a two-part fixture (that preferably screws, snaps or fits together), or rack. The sample tray fixture 31 preferably holds variety of sample trays such as a well plate (a 6-well, 24-well, 96-well, 384-well, 1536-well or other suitable well plate), a test tube rack, or any suitable container of a plurality of samples. The sample tray fixture 31 may alternatively be mounted to the sample arm joint 38, such that the sample tray fixture 31 merely defines the upper surface of the sample arm joint 38 so that a sample tray is seemingly connected to the sample arm joint 38 directly. In one preferred embodiment, the center of the sample tray is preferably positioned concentrically with the sample arm joint 38, such that a centrally located sample (or well) may be horizontally positioned by only actuating the base arm 20.

In the preferred embodiment, the sample tray fixture 31 preferably includes a plurality of bumpers 50. The bumpers 50 function to guide the sample tray into the sample tray fixture 31 and hold the sample tray. The bumpers 50 are preferably made of a resilient material, such as a rubber or a silicone. The bumpers 50 preferably cooperatively hold the sample tray in position through friction and/or by being dimensioned to closely define the perimeter of the sample tray. The bumpers may alternatively be made of a rigid material. The sample tray fixture 31 preferably has eight bumpers 50 arranged around a rectangular area defining the perimeter of a 96-well wellplate. Two bumpers 50 are preferably placed on each side of the rectangle, preferably near the corners of the rectangle. The bumpers could alternatively be a single structure lining the outside perimeter of the sample tray fixture 31. Alternatively, any number of bumpers could be used to adequately restrain a sample tray in a single position. The bumpers 50 are preferably conical in shape, where the angle of the cone functions to direct a wellplate into a singular position on the sample tray fixture 31.

As shown in FIG. 3, the horizontal linkage system 12 of the preferred embodiment additionally includes an arm positioning peg 56. The arm positioning peg 56 functions to stop the base arm 20 and/or sample arm 30 when rotated to a known position. When the base arm 20 and/or the sample arm 30 have been stopped by the arm positioning peg 56, the location and orientation of the horizontal linkage system 12 can be determined. Two arm positioning pegs 56 or any suitable number of arm positioning pegs 56 may additionally be used. In a first embodiment, the arm positioning peg 56 is preferably integrated into the base arm joint 28 and the sample arm joint 38 so that the rotation of the joint is mechanically stopped when at a known angle. One positioning peg 56 is preferably positioned on the base arm 20 to stop the rotation of the sample arm 30, while another positioning peg 56 is preferably positioned on the fixture 60 to stop the rotation of the base arm 20. Additionally, the positioning peg 56 may be a ratchet mechanism that stops an arm of the horizontal linkage system 12 when rotated in particular direction. In a second embodiment, the arm positioning pegs 56 may be physical stops projecting upwards to prevent rotation of an arm. In yet another embodiment, encoders may be placed on the joints of the base arm and sample arm. The encoder may be used to electronically monitor the position of the arms and electrically stop rotation of the base arm 20 or the sample arm 30 when the base arm 20 and/or sample arm rotate into a designated position. The horizontal linkage system 12 may alternatively incorporate any other suitable device or method to stop the base arm 20 and/or sample arm 30 when rotated to a known position.

As shown in FIG. 2, the drive system 14 of the preferred embodiment functions to actuate the base arm 20 and the sample arm 30. The drive system 14 preferably includes two motor/coupler subsystems 44. Each motor/coupler subsystem functions to rotate a joint (either the base arm joint 28 or the sample arm joint 38). The motor/coupler subsystem 44 preferably includes a driver motor 46 and a rotation coupler 48. The driver motor 46 functions to drive the motion. The two driver motors 46 of the motor/coupler subsystems 44 are preferably mounted on the underside of the base arm 20. The driver motors 46 may alternatively be place in any suitable position such as one on the base arm 20 and one on the sample arm 30. The driver motors 46 are preferably stepper motors, but alternatively may be servomotors or DC motors or any suitable actuator. The stepper motors preferably include encoders for measuring motor position, but external digital encoders may alternatively be attached to the driver motors 46 to monitor the driver motor 46 position, attached to the horizontal linkage system 12 to monitor the rotation angle of the base arm 20 and/or sample arm 30, or attached at any suitable location to sense position. The rotation coupler 48 of the motor/coupler subsystem 44 functions to transmit the rotation of the driver motor 46 into rotational work performed on either the base joint 28 or wellplate joint 38, without transforming the rotation of the driver motor 46 into some other form of motion, such as linear motion. This "transformationless" arrangement reduces the complexity, cost, and friction of the drive system 10. As used within this document, the term "transformationless" includes rotational motion that is converted into other rotational work, but excludes rotational motion that is converted to linear work. For example, the rotation of a driver motor 46 is translated into rotation of the base arm 20 about the base arm joint 28. The reduction in friction further enables the horizontal linkage system 12 to be rotated freely when the driver motors 46 are in a neutral state. Preferably, the rotation coupler 48 of the motor/coupler subsystem 44 is a belt and pulley. The belt and pulley couples one driver motor 46 to the base arm joint 28 and one driver motor 46 to the sample arm joint 38. Alternatively, gears, chains, sprockets, a drive shaft, or any other suitable device could be used to transmit the motion of the motor to the base arm joint 28 or sample arm joint 38. In a second embodiment, the driver motors 46 may be directly connected to the base arm joint 28 and the sample arm joint 38 without the use of a coupling device. In this second embodiment, the driver motors 46 preferably would be selected to have sufficient torque to rotate the base arm joint 28 and the sample arm joint 38 without the need for gears or pulleys.

The plate handler system 10 may additionally include a fixture 60. The fixture functions to mount the plate handler system 10 to a sampling device. The fixture 60 is preferably a rigid structure that is bolted to a chassis of the flow cytometer. The fixture is preferably removable from the sampling device (such that it may also be added to a sampling device). The fixture 60 may alternatively be integrated into the sampling device. For example, the fixture may additionally serve as part of the body of a sampling device. In a preferred embodiment, the fixture is preferably connected to the sampling device (e.g., a flow cytometer) and the vertical actuation system 40, and the horizontal linkage system 12 and drive system 14 are preferably connected to the vertical actuation system 40. The fixture 60 may alternatively be connected to the sampling device and the horizontal linkage system 12, and the vertical actuation system 40 is preferably connected to the horizontal linkage system 12. The fixture 60 may alternatively connect the plate handler system to any suitable frame or fixed reference link such as a table or surface.

Figure 4:
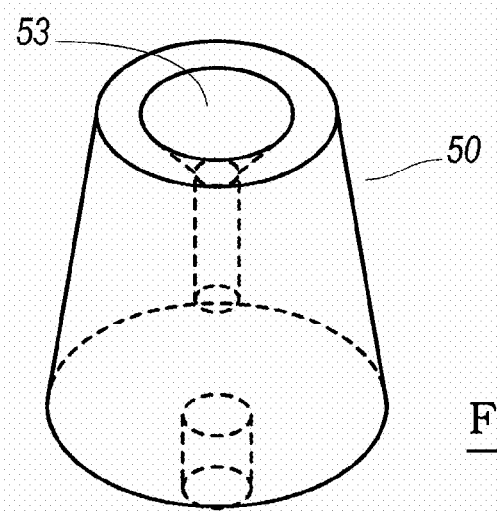
FIG. 4 is a detailed view of a positioning bumper.
Figure 5:
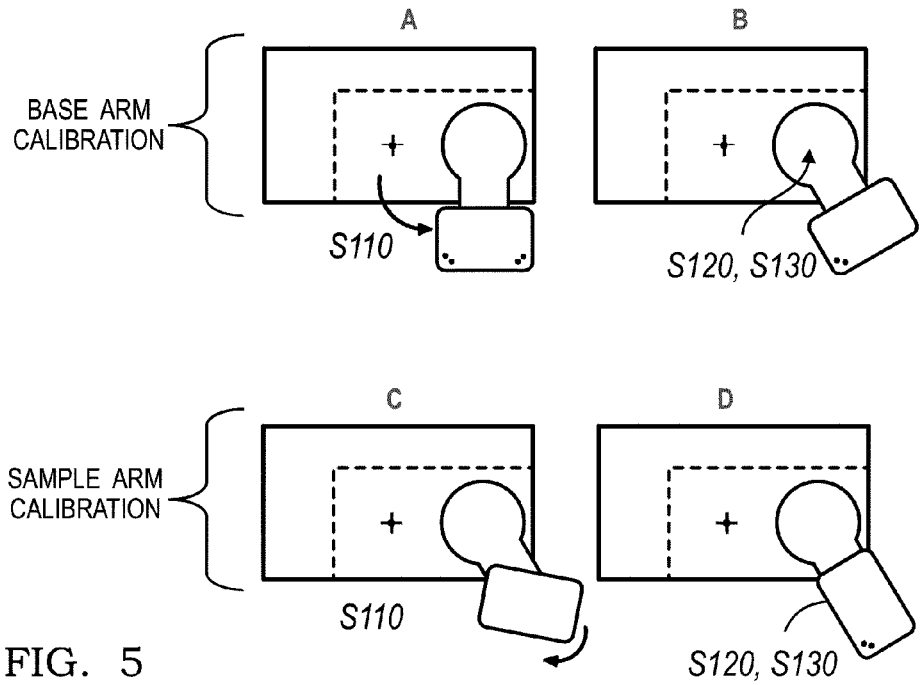
FIGS. 5A-5D are top views of a plate handler system attached to a flow cytometer illustrating a preferred method of calibrating a plate handler.
Figure 6:
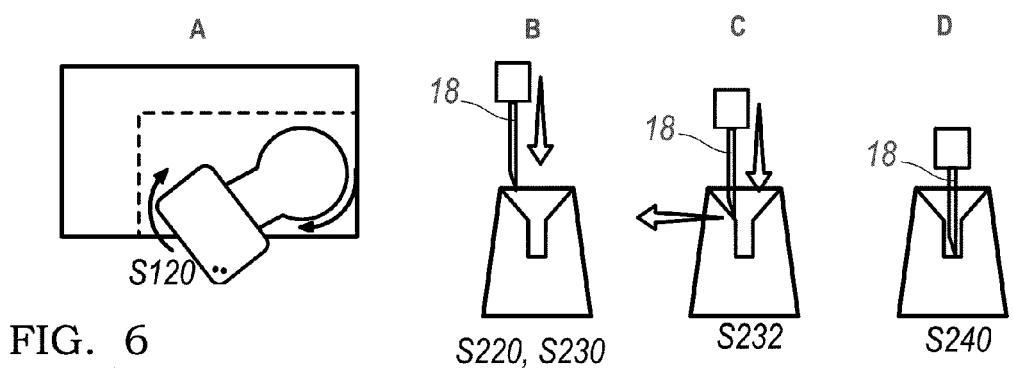
FIGS. 6A-6D is an illustrated representations of a preferred method of calibrating relative position between a drawtube and a sample tray, first showing a top view of a plate handler system attached to a flow cytometer (A) and then showing detailed views of a positioning bumper and a drawtube of a flow cytometer (C-D).

As shown in FIG. 4, the positioning bumper 52 of the preferred embodiment functions to determine the location of the drawtube relative to the wellplate. The shape of the positioning bumper 52 functions to guide a drawtube to a single point so that the position of the wellplate and the drawtube can be determined. The positioning bumper 52 is preferably a cylindrically shaped structure with one end of the cylinder defining a convex cavity 53 with a generally singular low point. Here convex cavity is preferably understood to describe a cavity that convexly extends into the positioning bumper 52, such that the walls of the positioning bumper 52 are concave. As an alternative description, the cavity 53 preferably extends into the positioning bumper 52 with a reducing cross section that terminates at a generally singular point. The cavity 53 is preferably conical shaped but may alternatively be an inverted pyramid, have parabolic or elliptical sides, or take on any suitable form that functions to terminate in a generally singular point. The size of the cavity 53 preferably provides enough space for the drawtube to be inserted down to the low point of the cavity 53. The shape and size of the walls defining the cavity 53 preferably slope downward directly to the singular low point such that they facilitate moving the drawtube toward the singular low point. The positioning bumper 52 may be attached to the sample arm 30, to one side of the sample tray fixture 31. Alternatively and/or additionally, the positioning bumper 52 may function as a bumper 50 used to define the area of the sample tray fixture 31. In one variation, the plate handler system 10 may include a plurality of positioning bumpers 52, which function to detect tilt or angle of the wellplate relative to the horizontal plane. Preferably, there are eight positioning bumpers 52 near each corner of the wellplate. Alternatively, there may be three or more positioning bumpers 52 to detect the tilt of the wellplate with the horizontal plane. In an alternative embodiment, the positioning bumper may be part of or attached directly to a sample tray. In an alternative embodiment, the positioning bumper may be part of a washing system, such as the washing system disclosed in U.S. Ser. No. 12/476,860 filed on 2 Jun. 2009 and entitled "Fluidic System with Washing Capabilities for a Flow Cytometer" (which is incorporated in its entirety by this reference). The positioning bumper 52 is preferably made of a low friction rigid plastic, or alternatively rubber, plastic, metal, or other suitable material.

2. Method of Using a Plate Handler

As shown in FIGS. 5A-5D, 6A-6D, and 7A-7C, the preferred method of using a plate handler includes a method of calibrating a plate handler. Additionally and/or alternatively, the preferred method of using a plate handler includes a method of calibrating relative position between a drawtube and a sample tray. The method of using a plate handler functions to calibrate the positioning of the horizontal linkage system and additionally the vertical actuation system for a plate handler system as described above.

As shown in FIGS. 5A-5D, the preferred method for calibrating a plate hander includes: rotating an arm of a horizontal linkage system S110, stopping the arm when the arm is positioned at a positioned peg S120, setting a coordinate system for the arm S130. The method functions to determine the relative position between a sampling device and a plate handler. The method preferably positions an arm in a calibration position to determine an origin for the position of the arm. As shown in FIG. 5, steps S110, S120, and S130 are preferably performed for a base arm and a sample arm, where the base arm and sample arm are substantially similar to the system described above. The steps S110, S120, and S130 may additionally be performed multiple times for a given arm with multiple positioning pegs to further calibrate the arm, such as by determining the range of motion (and encoder values) for a given arm. The method may additionally include actuating a vertical actuation system until a maximum distance is achieved and setting a coordinate system for a vertical axis.

Step S110, which includes rotating an arm of a horizontal linkage system, functions to move an arm in a horizontal linkage system to a calibration position. The calibration position is preferably at an extreme position in the range of motion of the vertical actuation system. For example, the calibration position may be when an arm is fully rotated clockwise. The arm is preferably rotated about a joint in either a clockwise position or counter clockwise position.

Step S120, which includes stopping the arm when the arm is positioned at a positioned peg, functions to place the arm in a calibration position. The arm positioning pegs 56 facilitate this step by functioning to stop the base arm 20 and the sample arm 30 in a known orientation so the relationship between the drive system and the horizontal linkage system can be determined. The arm is preferably stopped when the arm reaches a positioning peg. The position of a sample tray is preferably set in relationship to the horizontal linkage system, so by knowing the horizontal linkage system position the position of the sample tray is also known. The positioning peg is preferably a physical peg that obstructs the rotation of the arm. The positioning peg may alternatively be an electronic switch or button, an optical sensor, a physical structure or sensing device that may be used to stop the arm when a known position is reached.

Step 130 includes setting a coordinate system of the arm. Input from a positioning sensor, preferably an encoder on a motor is preferably read and set as the origin for the arm. The position preferably relates the relative position between the plate handler system and the sampling device (e.g., flow cytometer), but may alternatively relate the relative position of parts of the plate handler system to any suitable reference point.

As shown in FIGS. 6A-6D, the method of calibrating relative position between a drawtube and a sample tray of the preferred embodiment includes: rotating the horizontal linkage system such that the positioning bumper is generally under the drawtube S210; setting the driver motors of the drive system to neutral S220, actuating the vertical actuation system S230; stopping vertical actuation when the drawtube is at a low point of the positioning bumper S240; and setting position of a coordinate system S250. These steps function to position the drawtube and the wellplate such that their relative position is known. The positioning bumper preferably has a fixed position in relationship to a sample tray, and the positioning bumper is preferably substantially similar to the positioning bumper described above. In a second embodiment, steps S210 through S250 may be repeated for a plurality of positioning bumpers, which are preferably located on each corner of the sample tray. These repeated steps function to detect any tilt or angle of the wellplate relative to the horizontal plane.

Step S210, which includes rotating the horizontal linkage system such that the positioning bumper is under the drawtube, functions to position the positioning bumper in a location near the drawtube. Since the drawtube could have been moved or bent since the previous use of the plate handler system, the exact location of the drawtube is not necessarily known. Thus the horizontal linkage system is preferably rotated to the approximate position of the drawtube.

Step S220, which includes setting the drive motors of the drive system to neutral, functions to reduce the resistance of the horizontal linkage system so that the base arm and the sample arm may rotate relatively free of resistance or friction in later Steps S230 and S240. The drive motors are preferably put into neutral by releasing a holding current provided to the drive motors for the horizontal linkage system, but may alternatively be put into neutral by a clutch mechanism or by any other suitable device or method.

Step S230 and Step S240, which include actuating the vertical actuation system and stopping vertical actuation when the drawtube is at a low point of the positioning bumper, cooperatively function to move the drawtube and the wellplate into a known relative position. Step S230 preferably includes substep of guiding the drawtube into the low point with a slopped edge of the positioning bumper S232. Preferably, the drawtube makes contact with the convex cavity of the positioning bumper. The slope of the cavity and the vertical actuation of Step S230 result in a horizontal force. This horizontal force preferably rotates the horizontal linkage system 12 so the drawtube and the singular low point of the cavity 53 are aligned.

Step S250, which recites setting position of a coordinate system, functions to use the information of the position of the wellplate and the drawtube so that the plate handler system can accurately and precisely move the drawtube into and out of contact with the wellplate. The setting of the position preferably relates the relative position between a drawtube (even when bent) to that of a sample tray.

Figure 7:
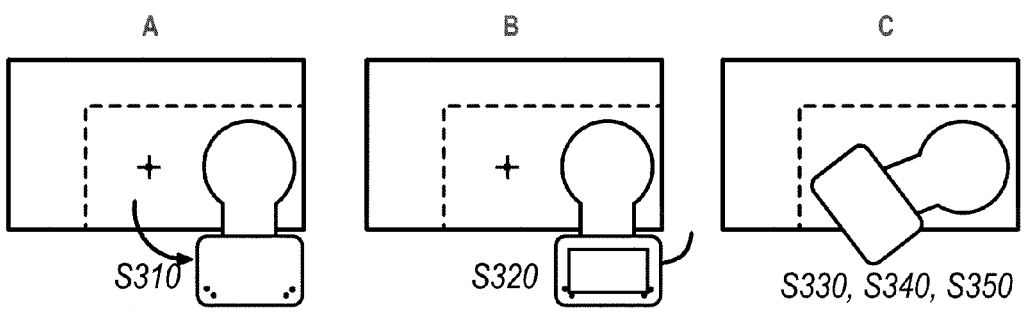
FIGS. 7A-7C is a top views of a plate handler system attached to a flow cytometer illustrating a preferred method of use of the plate handler.

As shown in FIGS. 7A-7C, the method of using a plate handler system of the preferred embodiment may additionally and/or alternatively include: rotating the horizontal linkage system 12 so the sample arm is outside of the flow cytometer S310; receiving a wellplate in the sample tray fixture S320; finding the location of the drawtube S330; moving the horizontal linkage system to a well S340; actuating the vertical actuation system to position the drawtube in a well S350. In Step S320, the receiving of a wellplate is preferably facilitated by the bumpers surrounding the sample tray. In Step S330, the location of the drawtube is preferably achieved by the position setting steps described above.

As a person skilled in the art of plate handlers will recognize from the previous detailed description and from the figures and claims, modifications and changes can be made to the preferred embodiments of the invention without departing from the scope of this invention defined in the following claims.

We claim:

1. A plate handler system for a sampling device with a drawtube comprising:
   a vertical actuation system configured to couple to the sampling device and adjust a vertical distance between the drawtube and a sample tray;
   a horizontal linkage system coupled to the vertical actuation system and configured to positions the sample tray in a horizontal plane, comprising:
   a base arm that rotates about a base arm joint, the base arm joint of the horizontal linkage system is coupled to the vertical actuation system and the base arm joint is concentric with a vertical actuation axis of the vertical actuation system; and
   a sample arm that receives the sample tray and that rotates about a sample arm joint coupled to the base arm, the sample arm joint is coupled to a distal portion of the base arm; and
   a drive system comprising a first drive motor that is coupled to the base arm and a second drive motor that is coupled to the sample arm, wherein the drive system is configured to independently rotate the base arm and the sample arm into a first configuration to position any a first sample of the sample tray between the drawtube and the sample arm and configured to independently rotate the base arm and the sample arm from the first configuration directly into a second configuration to position a second sample of the sample tray between the drawtube and the sample arm.

2. The plate handler system of claim 1, wherein the vertical actuation system includes a lead screw driven by a stepper motor.

3. The plate handler system of claim 1, wherein the drive system is a transformationless drive system that is configured to sequentially rotate each sample of the sample tray into alignment with the drawtube.

4. The plate handler system of claim 1, wherein the horizontal linkage system has two rotational degrees of freedom, and wherein horizontal linkage system is configured to manipulate a sample tray comprising samples arranged in a grid pattern.

5. The plate handler system of claim 4, wherein an axis of rotation provided by the first drive motor is fixed relative to an axis of rotation provided by the second drive motor.

6. The plate handler system of claim 5, the drive system further including a first belt that connects the first driver motor to the base arm joint and a second belt that connects the second driver motor to sample arm joint.

7. The plate handler system of claim 6, wherein the first drive motor and the second drive motor are mounted to the base arm.

8. The plate handler system of claim 5, including a first positioning peg that physically obstructs the rotation of the base arm at a first known orientation, and a second positioning peg that physically obstructs the rotation of the sample arm at a second known orientation.

9. The plate handler system of claim 1, wherein the sample arm includes a sample tray fixture configured to receive and hold the sample tray and to position the sample tray concentrically with the sample arm joint, such that rotation of the base arm and the sample arm into the first configuration to position the first sample of the sample tray between the drawtube and the sample arm and rotation of the base arm and the sample arm from the first configuration directly into the second configuration to position the second sample of the sample tray between the drawtube and the sample arm is enabled when the drawtube is rigidly fixed.

10. The plate handler system of claim 9 wherein the sample tray fixture includes a plurality of bumpers attached to the sample arm, wherein the bumpers are positioned to define the perimeter of the sample tray, and wherein the form of the bumpers is sloped to guide the sample tray into a singular position.

11. The plate handler system of claim 10, wherein the horizontal linkage system is configured to position a 96-well well plate.

12. The plate handler system of claim 10, further including a positioning bumper that includes a defined convex cavity with a low point.

13. The plate handler system of claim 12, wherein the positioning bumper also serves as one of the plurality of bumpers.

* * * * *